US011512032B2

(12) United States Patent
Schöffl

(10) Patent No.: US 11,512,032 B2
(45) Date of Patent: Nov. 29, 2022

(54) METHOD AND DEVICE FOR THE CATALYTIC CONVERSION OF A SUBSTANCE MIXTURE

(71) Applicant: OMV DOWNSTREAM GMBH, Vienna (AT)

(72) Inventor: Paul Schöffl, Gallneukirchen (AT)

(73) Assignee: OMV DOWNSTREAM GMBH, Vienna (AT)

( * ) Notice: Subject to any disclaimer, the term of this patent is extended or adjusted under 35 U.S.C. 154(b) by 0 days.

(21) Appl. No.: 16/976,554

(22) PCT Filed: Feb. 28, 2019

(86) PCT No.: PCT/AT2019/060065
§ 371 (c)(1),
(2) Date: Aug. 28, 2020

(87) PCT Pub. No.: WO2019/165486
PCT Pub. Date: Sep. 6, 2019

(65) Prior Publication Data
US 2020/0407299 A1 Dec. 31, 2020

(30) Foreign Application Priority Data
Feb. 28, 2018 (AT) .............................. A 50173/2018

(51) Int. Cl.
| C07C 29/60 | (2006.01) |
| B01D 19/00 | (2006.01) |
| B01J 8/02 | (2006.01) |
| B01J 23/30 | (2006.01) |
| B01J 23/652 | (2006.01) |
| B01J 27/188 | (2006.01) |
| B01J 29/16 | (2006.01) |
| B01J 35/02 | (2006.01) |
| B01J 35/10 | (2006.01) |
| B01J 37/00 | (2006.01) |
| B01J 37/02 | (2006.01) |
| B01J 37/04 | (2006.01) |

(52) U.S. Cl.
CPC .......... *C07C 29/60* (2013.01); *B01D 19/0036* (2013.01); *B01J 8/0278* (2013.01); *B01J 8/0285* (2013.01); *B01J 23/30* (2013.01); *B01J 23/6527* (2013.01); *B01J 27/188* (2013.01); *B01J 29/166* (2013.01); *B01J 35/026* (2013.01); *B01J 35/1057* (2013.01); *B01J 35/1061* (2013.01); *B01J 37/0018* (2013.01); *B01J 37/024* (2013.01); *B01J 37/0205* (2013.01); *B01J 37/04* (2013.01); *B01J 2208/00106* (2013.01); *B01J 2208/00849* (2013.01)

(58) Field of Classification Search
CPC ....... C07C 29/60; B01J 8/0278; B01J 8/0285; B01J 23/30; B01J 23/6527; B01J 27/188; B01J 35/026; B01J 35/1061; B01J 37/0018
See application file for complete search history.

(56) References Cited

U.S. PATENT DOCUMENTS

| 8,075,642 B2 | 12/2011 | Dumesic et al. |
| 8,507,736 B2 | 8/2013 | Hulteberg et al. |
| 8,946,458 B2 | 2/2015 | Blank et al. |
| 2009/0005614 A1 | 1/2009 | Hulteberg et al. |
| 2009/0255171 A1 | 10/2009 | Dumesic et al. |
| 2010/0317901 A1 | 12/2010 | Chaudhari et al. |
| 2014/0101988 A1 | 4/2014 | Feng et al. |

FOREIGN PATENT DOCUMENTS

| CN | 101054339 | 10/2007 |
| CN | 103706392 | 4/2014 |
| CN | 105688906 | 6/2016 |
| DE | 10 2008 026 583 | 12/2009 |
| EP | 2 016 037 | 10/2015 |
| JP | H08-165260 | 6/1996 |
| JP | H09-255326 | 9/1997 |
| JP | 2001-524541 | 12/2001 |
| JP | 2005-15323 | 1/2005 |
| JP | 2007-326849 | 12/2007 |
| JP | 2008-019397 | 1/2008 |
| JP | 2008-074764 | 4/2008 |
| JP | 2010-018602 | 1/2010 |
| JP | 2010-539300 | 12/2010 |
| JP | 2013-224267 | 10/2013 |
| WO | WO 2008/077205 | 7/2008 |
| WO | WO 2013/163561 | 10/2013 |
| WO | WO 2017/208497 | 12/2017 |

OTHER PUBLICATIONS

Priya et al., metal-acid bi-functional catalysts for selective hydrogenolysis of glycerol, (Applied Catalysis A: General 498 (2015) 88-98).*
Austrian Search Report dated Oct. 31, 2018 issued in Austrian Patent Application No. A 50173/2015, 5 pp.
International Search Report dated May 14, 2019 issued in PCT International Patent Application No. PCT/AT2019/060065, 5 pp.
Lin, Xufeng et al., "Hydrogenolysis of Glycerol by the Combined Use of Zeolite and Ni/Al$_2$O$_3$ as Catalysts: A Route for Achieving High Selectivity to 1-Propanol," Energy & Fuels, vol. 28, No. 5, May 15, 2014, pp. 3345-3351.
Wang, Mangpan et al., "Catalytic Transformation of Glycerol to 1-propanol by Combining Zirconium Phosphate and Supported Ru Catalysts," RSC Advances, vol. 6, Mar. 16, 2016, pp. 29769-29778.
Japanes Office Action dated Dec. 21, 2021 issued in Japanese Patent Application No. 2020-545345 and English translation, 20 pp.

* cited by examiner

*Primary Examiner* — Jafar F Parsa
(74) *Attorney, Agent, or Firm* — Nixon & Vanderhye P.C.

(57) ABSTRACT

In a method, device, catalyst and a method for producing a catalyst for the catalytic conversion of a substance mixture containing glycerol to propanol in a fixed-bed reactor, substrates of the catalyst have inorganic materials and/or metal oxides. The substrates have a pore diameter at the surface of between 10 and 25 angstroms, preferably between 12 and 20 angstroms, particularly preferably 15 angstroms.

20 Claims, 1 Drawing Sheet

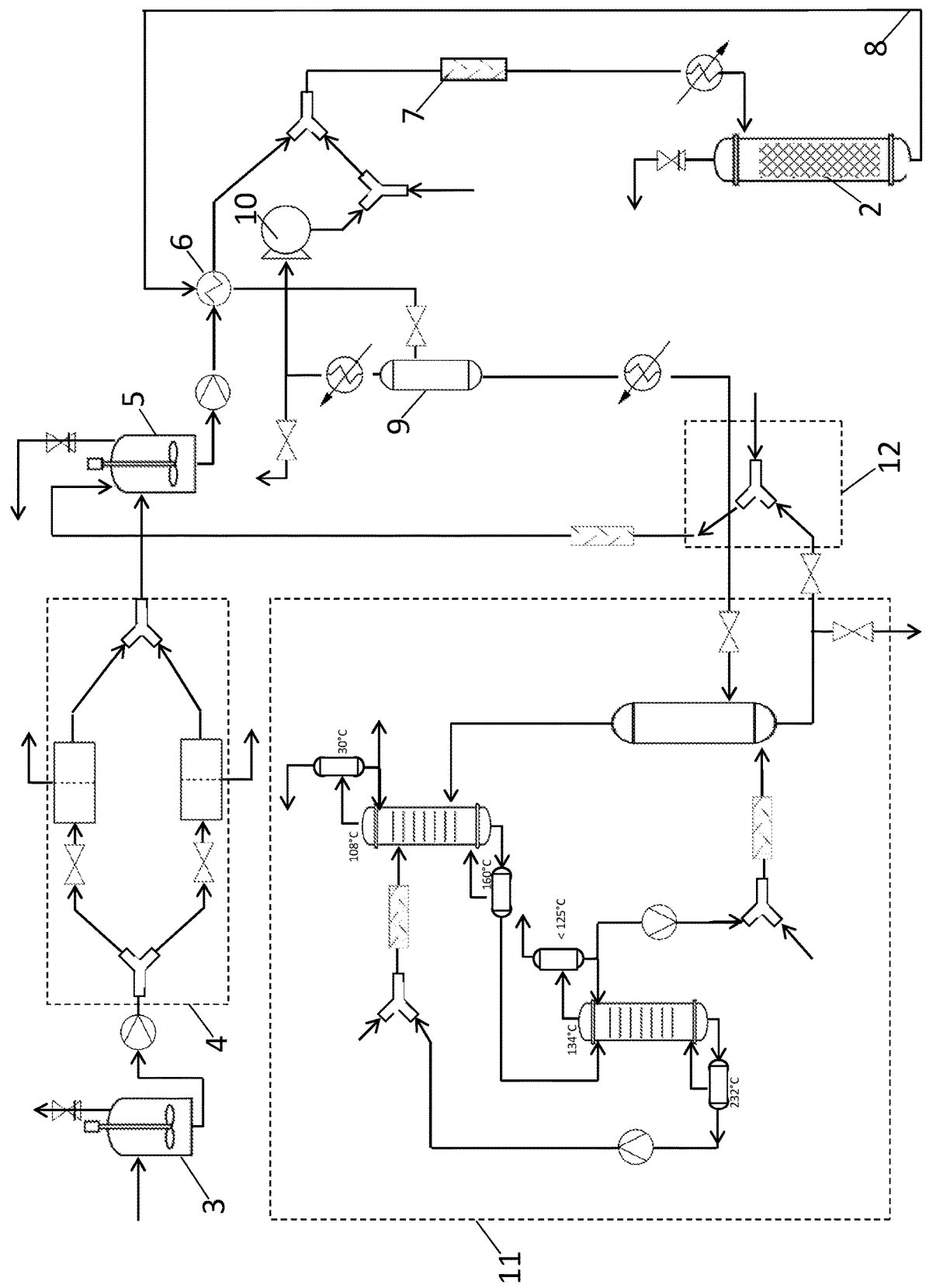

METHOD AND DEVICE FOR THE CATALYTIC CONVERSION OF A SUBSTANCE MIXTURE

This application is the U.S. national phase of International Application No. PCT/AT2019/060065 filed Feb. 28, 2019 which designated the U.S. and claims priority to Austrian Patent Application No. A 50173/2018 filed Feb. 28, 2018, the entire contents of each of which are hereby incorporated by reference.

The invention relates to a method and a device for the catalytic conversion of a substance mixture containing glycerol to propanols in a fixed-bed reactor, wherein substrates of the catalyst comprise inorganic materials and/or metal oxides. Furthermore, the invention relates to a catalyst and a method for producing a catalyst for the catalytic conversion of a substance mixture containing glycerol to propanols in a fixed-bed reactor, wherein substrates of the catalyst comprise inorganic materials and/or metal oxides.

The demand for energy and in particular for fuels has been increasing for a long time due to industrialisation and modernisation. For this reason, a large number of directives have been issued, for example by the European Union, to reduce the emission of greenhouse gases from fossil fuels. Fossil fuels are being partly replaced by renewable fuels. In the EU, for example, this is regulated by the now amended version of the Renewable Energy Directive (RED II), which stipulates that a proportion of 14 percent of energy must come from renewable raw materials. A further objective is the addition of advanced biofuels in an amount of 0.2e % (energy percentage) from 2022, 1e % from 2025, and 3.5e % in 2030 to fuels in the transport sector, with these only being permitted to be produced from a limited list of raw materials specified in the directive. The advantage of advanced biofuels is that they do not compete directly with food production and therefore only lead to reduced indirect land use change (ILUC). Currently, there are only a few commercial methods for the production of these components. Many of the processes are only being tested on a small scale, and therefore components of this kind are expensive and difficult to acquire in sufficient quantities.

Crude glycerol is a listed starting material according to the EU directive. From biodiesel production, about 10 weight percent of glycerol is obtained as a by-product in the form of crude glycerol. Crude glycerol is usually contaminated, for process-related reasons, with sodium chloride, water, methanol, sulphates, monoglycerides, diglycerides, ash, insufficiently separated fat residues and other substances. The term "crude glycerol" within the meaning of the invention is understood to mean a liquid mixture with a glycerol portion of at least 60 wt. %, which mixture additionally also has a mineral portion, i.e. a portion of cations such as sodium, potassium, calcium, magnesium as well as chlorine and phosphorus, of from 1 wt. % to 10 wt. % and a water portion of more than 5 wt. %. Crude glycerol has a great potential to contribute significantly to the production of advanced biofuels, inter alia due to its favourable price, liquid nature and good availability. From an energy point of view, it is most advantageous to produce the corresponding mono-alcohols, i.e. 1-propanol (n-propanol) and/or 2-propanol (isopropanol), from glycerol (propane-1,2,3-triol) on the basis of stoichiometry. In addition, due to the higher energy density of advanced bio-propanols, a relatively smaller amount is required as an admixture component than is the case with advanced bio-ethanol. The most promising starting material for the production of advanced bio-propanols is crude glycerol as a by-product of biodiesel production.

Many different processes for the conversion of glycerol into high-value or useful chemicals have already been tested and analysed, such as the oxidation, esterification and hydrogenolysis of glycerol.

For example, U.S. Pat. No. 8,507,736 B2 shows a method for producing short-chain alcohols from glycerol, which is produced as a by-product of biodiesel production. Specifically, the product stream can comprise a mixture of ethanol, methanol and propanol, with propanol accounting for more than 50 percent of the total mass of monohydric alcohols in the product stream. Processing can be carried out in a single reaction step that includes both dehydration and hydrogenation. The catalyst used may be a mixture of a dehydration catalyst and a hydrogenation catalyst, the former of which may contain oxides of tungsten and zirconium and the latter of which may contain a metal from the platinum group. The reaction in a single step shall be carried out at about 300° C.

Furthermore, U.S. Pat. No. 8,946,458 B2 discloses a series of catalysts and methods and reactor systems for processing oxygenous hydrocarbons. Particular mention is made of the use of glycerol as a by-product from biodiesel production as an application. The products obtained from this include 1-propanol and acetone, amongst others. A heterogeneous hydrodeoxygenation catalyst (HDO) is used for the reaction, with a large number of different catalysts being described. Regarding doping, it is mentioned that a bimetallic catalyst with platinum and molybdenum on a tungsten-zirconium support can be used. A range between 100° C. and 300° C. is given as the reaction temperature at a pressure of between 4 and 140 bar.

EP 2 016 037 BI shows a method for processing an aqueous feed, which also comprises glycerol, in a single catalytic process and using in-situ generated hydrogen to produce, inter alia, alcohols, which include in particular ethanol and propanol. The catalyst support may be silicon or zirconium, which may be treated with tungsten. In this context, it is mentioned that the use of oxides of zirconium, inter alia, is preferred. The catalyst may also contain a transition metal, for example platinum or rhodium. The method takes place in two chemical steps, for which different—but overlapping—temperature ranges of between 80° C. and 400° C. and between 100° C. and 300° C. are specified.

CN 101054339 D4 shows a method for processing the biodiesel by-product glycerol to n-propanol in a continuous process with a fixed-bed catalyst with a number of tubes. The catalyst support used includes ZrO2, with tungsten, rhodium, molybdenum and platinum, inter alia, as active components. The reaction temperature is between 180 and 360° C.

Further methods are disclosed, for example, in U.S. Pat. No. 8,075,642 B2, DE 10 2008 026 583 A1, "Catalytic transformation of glycerol to 1-propanol by combining zirconium phosphate and supported Ru catalysts" by Wang et al. in RCS Advances vol. 6, 16 Mar. 2016, pages 29769-29777, CN 103 706 392 B, "Hydrogenolysis of Glycerol by the Combined Use of Zeolite and Ni/Al2O3 as Catalysts: A Route for Achieving High Selectivity to 1-Propanol" by Xufeng Lin et al. in Energy & Fuels vol. 28, No. 5, 15 May 2014, pages 3345-3351, and WO 2013/163561 A1.

However, all currently available methods have one or more essential disadvantages. It is usually only possible to directly process refined glycerol, but not crude glycerol or impure glycerol. In order to obtain refined glycerol from crude glycerol, impurities must be removed, although not all of the glycerol produced can be further processed into refined glycerol. Often, the only purification step is to recover methanol from the crude glycerol. Due to the absence of an extensive purification process, crude glycerol is much more inexpensive than refined glycerol. In particular, there are no known catalysts or methods for the production of such catalysts that meet these requirements satisfactorily, thus preventing continuous operation. Prior-art techniques may, for example, deposit salts or sulphur on the catalyst and thus reduce its effectiveness. Furthermore, all methods are complex, have low selectivity or a low conversion rate and/or are expensive to implement.

An objective of the invention is thus to overcome all or some of the above-mentioned disadvantages and in particular to create a method and a device and a catalyst and a method for the production of a catalyst with which both the conversion of glycerol and the selectivity to the product propanol are high. Another objective is to further process crude glycerol into a fuel or an admixable fuel component without costly preliminary purification or preparation. A further objective is to immobilise the catalytically active compounds on the substrate of the catalyst in order to prevent these catalytically active substances, which often are easily water-soluble, from being dissolved out during the course of the process. Furthermore, it should be possible to transfer the proposed methods from the laboratory to a large-scale plant in sufficient dimensions, i.e. it should allow for appropriate upscaling. Furthermore, conditions should be achieved under which the production of by-products, such as dimerisation products and ketones, is limited.

This is achieved by the subject matter and the method of the independent claims.

In particular, this is achieved by a method and a device for converting a substance mixture containing glycerol to propanols as described above, wherein the substrates of the catalyst comprise a pore diameter at the surface of between 10 and 25 angstroms, preferably between 12 and 20 angstroms, particularly preferably substantially of 15 angstroms. Furthermore, this is achieved by a catalyst for converting a substance mixture containing glycerol to propanols as described above, wherein the substrates of the catalyst comprise a pore diameter at the surface of between 10 and 25 angstroms, preferably between 12 and 20 angstroms, particularly preferably substantially of 15 angstroms, and by a method for producing a catalyst for converting a substance mixture containing glycerol to propanols as described above, wherein base materials for production of the substrate of the catalyst comprise a pore diameter at the surface between 10 and 25 angstroms, preferably between 12 and 20 angstroms, particularly preferably substantially of 15 angstroms, or the base material for production of the substrates of the catalyst comprises USY zeolites, wherein the USY zeolites are dealuminated so that the substrates of the catalyst comprise a pore diameter at the surface between 10 and 25 angstroms, preferably between 12 and 20 angstroms, particularly preferably substantially of 15 angstroms. Said pore diameters may also be provided inside the substrates or in a part thereof.

Tests have shown that, by this production method and by selecting a substrate with such pore sizes, the catalytically active substances, for example silicotungstic acid, which are otherwise usually highly water-soluble, are immobilised well on the catalyst substrate. This means, for example, that in the case of a reaction which takes place in the liquid, aqueous phase, for example under a pressure of 25 to 50 bar, the catalyst, in particular the dehydration catalyst, cannot be dissolved by hydration, i.e. dissolution with water, but remains stably immobilised and thus the active centres are freely accessible and retained despite an aqueous reaction.

Advantageously, the reaction should take place in a single step. Previous research has suggested that a combined catalyst system is necessary, since, in the reaction, the dehydration must be followed by hydrogenation. Therefore, it is advantageous to combine two different catalyst systems on one substrate so that the reaction can be carried out in a single step. The immobilisation of the catalytically active substances, in particular the dehydration catalyst, for example silicotungstic acid, is most likely due on the one hand to physicochemical interactions, presumably adsorptive Van-der-Waals forces, and on the other hand to the ideal pore diameter and thus the inaccessibility of the catalytically active substance. Furthermore, the catalytically active substance, in particular the dehydration catalyst, is deposited preferably near the surface due to the molecular size, with the deposition taking place in particular in coarse pores, and, in contrast to the hydrogenation catalyst, the dehydration catalyst being unable to penetrate further into the substrate.

With regard to the method for converting a substance mixture containing glycerol to propanols, it is advantageous if the substrates of the catalyst used are extrudate pellets and preferably ceramic. By extruding and subsequently conditioning catalyst pellets, organic binders advantageously volatilise on the substrate surface almost without residue, and the pellets acquire a corresponding strength.

Preferably, the conversion of the substance mixture containing glycerol to propanols is carried out continuously with the catalyst described above in a fixed-bed reactor. In this way, the highest possible glycerol throughput can be achieved, and at the same time a very high conversion to propanols of over 85% can be achieved. Due to the immobilization of the otherwise water-soluble dehydration catalyst, made possible by the special substrates of the catalyst, the catalyst activity is maintained at this high level in the long term and catalyst change intervals and thus plant downtimes are reduced to a minimum. The fixed-bed reactor is preferably single-stage.

In a preferred variant of the method, mixed oxides of silicon, tungsten, zirconium and/or aluminium, preferably zirconium dioxide, zeolites (preferably synthetic aluminosilicates and aluminophosphates), preferably VFI zeolites or VPI-5 zeolites, dealuminated USY zeolites and/or aluminium dioxide are used as substrate for the catalyst. Such substrates have proven to be particularly favourable over the course of test series.

It is also advantageous if the catalyst comprises a platinum doping. According to the prior art, immobilising platinum as second catalytically active substance of the catalyst on the substrate is no problem. According to the current prior art, $ZrO_2$ is not an advantageous catalyst for the conversion of glycerol to propanols, but as a support material for the catalyst it is advantageous in many reactions due to its high thermal stability, great hardness and good stability under reducing conditions. Acid centres are presumably necessary for the dehydration step, in which acetol and 3-hydroxypropionaldehyde are the possible products of glycerol. Phosphotungstic acid could also be a possibility for the dehydration step. Advantageously, a metal catalyst is responsible for the hydrogenation of the intermediate products. Precious metals such as platinum are known to be hydrogenation catalysts, presumably because they activate hydrogen molecules. Ruthenium is also possible because it is not as sensitive to sulphur as other catalysts. Base metals (non-precious metals) such as copper or nickel are also possible.

In general, the catalyst should comprise an optimum ratio of acid centres and hydrogenation centres, and advantageously should be as resistant as possible to catalyst poisoning. In addition to the substrate, the composition of the catalyst preferably consists of a proportion of platinum, ruthenium, copper or nickel of from 0.5 to 5 wt. %, preferably between 1 and 3 wt. %, particularly preferably substantially 1.5 wt. %, and of silicotungstic acid or phosphotungstic acid between 5 and 20 wt. %, preferably between 7.5 and 15 wt. %, particularly preferably substantially 12 wt. %.

As starting material, i.e. as a substance mixture containing glycerol, it is possible to use crude glycerol, technical glycerol and/or purified glycerol. It is particularly advantageous if crude glycerol is used, as it is characterised by a low price and is a by-product of various methods. Furthermore, the (legal) guidelines for advanced biofuels, especially according to Directive (EU) 2015/1513, Annex IX, Part A, also known as "RED II", usually include only this substance. In terms of glycerol content and proportion of impurities, technical glycerol is between crude glycerol and purified glycerol.

Preferably, in a first step of the method, the substance mixture containing glycerol is removed from a storage container and advantageously filtered, in particular to remove any undissolved solids and undesirable accompanying substances contained therein, depending on the quality of the substance mixture containing glycerol, in particular depending on the degree of contamination. The substance mixture containing glycerol may optionally be centrifuged before or after this step. The (preferably pre-treated) substance mixture containing glycerol is preferably then mixed with water and diluted, the glycerol content preferably being adjusted to between 5 and 80 percent, particularly preferably to between 10 and 60 percent, even more preferably to between 15 and 50 percent, depending on the desired product yield structure, the glycerol content being adjusted to between 0.7 and 0.9 times the desired stoichiometrically possible concentration (amount of substance) of 1-propanol in the end product. If this step is carried out, the substance mixture containing glycerol hereinafter refers to the mixture of the original (preferably pre-treated) substance mixture containing glycerol with water obtained in this step.

In an advantageous method step, the substance mixture containing glycerol is preferably heated via a heat exchanger, preferably an economiser for quasi-adiabatic reaction execution, preferably to between 150 and 300° C., particularly preferably to between 190 and 250° C., even more preferably to substantially 220° C. Hydrogen is preferably added to the substance mixture containing glycerol, preferably in a static mixer, with hydrogen preferably being adjusted in excess to 10 to 60 times the desired, stoichiometrically possible concentration (amount of substance) of 1-propanol in the end product.

If this step is carried out, the substance mixture containing glycerol (in addition to any previous additives and purifications) refers to the substance mixture mixed with hydrogen.

The substance mixture containing glycerol is then passed through a, preferably continuous, catalytic fixed-bed reactor. The process fluid (the reacted substance mixture containing glycerol) is preferably led after the fixed-bed reactor to the heat exchanger for heat input. The energy from the process heat is advantageously sufficient to ensure the preheating of the substance mixture containing glycerol before the reaction in the fixed-bed reactor, i.e. no external reaction energy has to be supplied and/or removed (except when starting up the plant); the reaction is thus advantageously adiabatic.

Subsequently, the process medium is advantageously expanded, preferably to between 0.2 and 0.02 times, particularly preferably to between 0.1 and 0.03 times, even more preferably to substantially 0.04 times the original pressure. Then, preferably hydrogen is recovered from the reacted substance mixture via a separator device, the recovered hydrogen being recompressed via a compressor and added to the fresh hydrogen which was added to the substance mixture before the reaction in the fixed-bed reactor. The proportion of the recovered hydrogen in the total amount of hydrogen used for the reaction is preferably between 50 and 99 percent, particularly preferably between 70 and 97 percent.

In further advantageous method steps, an organic target fraction can be obtained from the reacted substance mixture, preferably physically, particularly preferably by distillation, i.e. the process water contained and also formed as a by-product are removed and pure propanols are obtained. Both 1-propanol and 2-propanol are preferably obtained. The product stream preferably contains between 10 and 22 wt. % of 2-propanol and between 60 and 85 wt. % of 1-propanol, for example 20 wt. % of 2-propanol and 70 wt. % of 1-propanol. However, only one of the two might also be obtained. Preferably, 1-propanol and/or 2-propanol are/is obtained via a treatment cascade by first removing water from the substance mixture reacted in the fixed-bed reactor and obtaining pure propanols, the separated process water being added to fresh water in a water mixer, which is usually a conventional mixer, and the water mixture being used particularly preferably in the method at an earlier point, particularly for mixing with the mixture containing glycerol in the mixer, and even more preferably the recovered process water having a proportion of between 80 and 100 percent, preferably between 90 and 100 percent, of the total water used in the method. Alternatively or additionally, the obtained organic target fraction can also be used in a further method step to build up longer-chain hydrocarbons, i.e. to oligomerise them.

Preferably, the reaction is carried out in the fixed-bed reactor at a temperature between 150 and 300° C., preferably between 190 and 250° C., particularly preferably between 210 and 230° C. Experiments have shown that at lower temperatures the conversion was low, whereas high temperatures caused a lower selectivity for propanols, and with the temperature intervals mentioned, especially with the interval between 210 and 230° C., the efficiency was good in terms of the optimal ratio between energy input, conversion and selectivity.

In a preferred variant, the conversion is carried out in the fixed-bed reactor at a pressure between 10 and 100 bar, preferably between 15 and 75 bar, even more preferably between 25 and 50 bar, since under these conditions a particularly good efficiency can also be achieved.

In particular, the product stream resulting from the method according to the invention comprises between 0.1 and 5 wt. % MeOH, between 3 and 6 wt. % EtOH, between 10 and 22 wt. % 2-propanol, between 3 and 6 wt. % acetone, and between 60 and 85 wt. % 1-propanol. A glycerol content in the product of less than 0.05 wt. % is preferably achieved.

In one embodiment, crude glycerol was used, the chemical analysis of which showed the following composition:
Na: 0.13 wt. %
Ca: <0.01 wt. %
K: 0.61 wt. %
Al: <0.001 wt. %
Si: <0.001 wt. %
Fe: 0.0004 wt. %

Cr: <0.0001 wt. %
Ni: <0.0001 wt. %
S: 0.5548 wt. %
Cl: <0.0001 wt. %
V: <0.001 wt. %
Zn: <0.001 wt. %
carbon: 32.30 wt. %
hydrogen: 9.80 wt. %
water: 14.0 wt. %
glycerol content: 79.9 wt. %
acid value: 0.45 mg KOH/g In this embodiment, the process was carried out with a WHSV (Weight Hourly Space Velocity) of 0.80 per h, a ratio of hydrogen to glycerol of 33 mol/mol, an average reaction temperature of 220° C., with the temperature, distributed over the reactor, being between 217 and 225° C., and a pressure of 50 bar. This resulted in the following product composition:

MeOH: 0.3 wt. %
EtOH: 5.6 wt. %
2-propanol: 13.9 wt. %
Acetone: 5.5 wt. %
1-propanol: 74.6 wt. %

Traces of other analytes, inorganic constituents and water were removed by extractive distillation.

The conversion depends on the WHSV or the molar ratio of hydrogen to glycerol and the temperature. As an example, the following conversions are achieved:

Example 1: WHSV: 0.07 per h; ratio of hydrogen to glycerol: 133 mol/mol

| Temperature [° C.] | 200 | 225 | 250 |
|---|---|---|---|
| Conversion [%] | 100 | 100 | 100 |

Example 2: WHSV: 0.07 per h; ratio of hydrogen to glycerol: 66 mol/mol

| Temperature [° C.] | 200 | 225 | 250 |
|---|---|---|---|
| Conversion [%] | 75 | 100 | 100 |

Example 3: WHSV: 0.15 per h; ratio of hydrogen to glycerol: 32 mol/mol

| Temperature [° C.] | 200 | 225 | 250 |
|---|---|---|---|
| Conversion [%] | 58 | 99 | 100 |

Example 4: WHSV: 0.21 per h; ratio of hydrogen to glycerol: 33 mol/mol

| Temperature [° C.] | 200 | 225 | 250 |
|---|---|---|---|
| Conversion [%] | 22 | 80 | 96 |

The conversion (in %) was calculated as (glycerol (input)−glycerol (output))/glycerol (output)*100. Higher temperatures favour higher conversions. Similarly, higher molar ratios favour higher conversions. More than 80 wt. % of glycerol can be converted to propanols, preferably more than 90 wt. %.

With reference to the device according to the invention for the catalytic conversion of a substance mixture containing glycerol in a fixed-bed reactor to propanols, it is advantageous if the substrates of the catalyst are preferably ceramic extrudate pellets.

Furthermore, it is advantageous if the substrates of the catalyst are mixed oxides of silicon, tungsten, zirconium and/or aluminium, preferably zirconium dioxide, aluminosilicate zeolites and/or aluminophosphate zeolites, preferably VFI zeolites and/or VPI-5 zeolites, dealuminated USY zeolites and/or aluminium dioxide. It may also be advantageous if the substrate comprises a platinum doping. The fixed-bed reactor is further preferably suitable for continuous operation.

The device preferably comprises one or more of the following objects:
  a storage container for the substance mixture containing glycerol,
  a filter device for removing undissolved solids and/or undesirable accompanying substances contained in the substance mixture containing glycerol,
  a first mixer for diluting the substance mixture containing glycerol with water,
  a heat exchanger, preferably an economiser, for heating the substance mixture containing glycerol,
  a preferably static second mixer for adding hydrogen to the substance mixture containing glycerol,
  a line for returning the substance mixture converted in the fixed-bed reactor to the heat exchanger,
  a separation device for recovering hydrogen from the substance mixture reacted in the fixed-bed reactor and preferably a compressor for compressing the recovered hydrogen, which can be fed to a starting hydrogen and mixed with it,
  a treatment cascade 11, which separates the pure propanols and the process water by means of extraction agents, the extraction agents for the extraction circuit being recovered in the treatment cascade and the process water preferably also being recovered, advantageously for reuse for the production of a diluted substance mixture containing glycerol in the mixer.

With reference to the catalyst according to the invention for the catalytic conversion of a substance mixture containing glycerol to propanols in a fixed-bed reactor, it is advantageous if the substrates, preferably ceramic, are extrudate pellets. Furthermore, it is advantageous if the substrates of the catalyst comprise mixed oxides of silicon, tungsten, zirconium and/or aluminium, preferably zirconium dioxide, aluminosilicate and/or aluminophosphate zeolites, preferably VFI zeolites and/or VPI-5 zeolites, dealuminated USY zeolites and/or aluminium dioxide and preferably platinum doping and/or the catalyst is suitable for continuous operation of the fixed-bed reactor.

With reference to the method according to the invention for producing a catalyst for the catalytic conversion of a substance mixture containing glycerol to propanols in a fixed-bed reactor, it is essential that the substrate base materials already comprise a suitable pore size, in particular a pore diameter at the surface of between 10 and 25 angstroms, preferably between 12 and 20 angstroms, particularly preferably substantially of 15 angstroms, so that, ultimately, the pore diameter at the surface of the substrates at their surface is between 10 and 25 angstroms, preferably between 12 and 20 angstroms, particularly preferably substantially of 15 angstroms. If the pore diameter of the base materials is not yet within the corresponding range, as is the case with USY zeolites, it is necessary to first bring the pore diameter to a suitable size by suitable measures, in particular by dealumination. USY zeolites are what are known as ultra-stabilised (Y-) zeolites. These actually have a too small pore size, but are mechanically extremely stable. This property is particularly relevant in up-scaling, for example due to the high reactors and the compressive stress caused by the inherent weight. If these USY zeolites are dealuminated, i.e. a defined part of the aluminosilicate composite is subsequently chemically removed, the pore size can be appropriately expanded, in particular to the aforementioned desired pore diameter on the surface of the substrate. In summary, the pore size, mechanical stability and the potential for surface interactions or physisorption for immobilisation of, for example, the silicotungstic acid are the decisive criteria for the selection of the substrate material. With reference to the use of USY zeolites, which originally do not yet have the correct pore size, as the base material for the production of the substrates of the catalyst, it is advantageous if dealumination is carried out with a complexing agent, especially EDTA.

It is advantageous if mixed oxides of silicon, tungsten, zirconium and/or aluminium, preferably zirconium dioxide, aluminosilicate and/or aluminophosphate zeolites, preferably VFI zeolites and/or VPI-5 zeolites, dealuminated USY zeolites and/or aluminium dioxide are used as base materials for the substrates (the support material) of the catalyst.

Preferably, organic binders are first worked into base materials, which are preferably in powder form, and these are then homogeneously kneaded to form a base compound, and the organic binders are then burnt out substantially without residue, particularly substantially on the substrate surface. A dispersion, particularly preferably a nano-dispersion, of polymers, preferably polystyrene, and water is preferably used as the organic binder, the polymer content of the dispersion preferably being less than 5 wt. %, particularly preferably less than 1 wt. %. Subsequently, pellets are extruded from the basic mass, preferably under a pressure between 5 and 120 bar, particularly preferably between 20 and 100 bar, even more preferably between 40 and 80 bar, to a diameter between 1 and 8 mm, preferably between 2 and 6 mm, particularly preferably between 3 and 4 mm and/or a length between 0.25 and 4 cm, preferably between 0.4 and 3 cm, particularly preferably between 0.5 and 2 cm, and the pellets are preferably conditioned at a temperature between 400 and 1000° C., preferably between 500 and 750° C., even more preferably at substantially 600° C. for a period between 24 and 168 h, preferably between 36 and 96 h, even more preferably for substantially 48 h.

Furthermore, it is advantageous if the extruded substrate pellets are impregnated with platinum, wherein per 1000 g substrate material preferably between 0.5 and 3 litres, preferably substantially 1.5 litres of aqueous solution of between 15 and 300 mmol/l, preferably substantially 75 mmol/l of H2PtCl6.6H2O are used for impregnation. The pellets are then preferably dried, this being carried out at a temperature between 60 and 120° C., preferably substantially 90° C. The pellets are then advantageously calcined at between 250 and 450° C., preferably substantially 350° C. for between 6 and 24 hours, preferably substantially 12 hours.

Further advantageous is a subsequent impregnation of the platinum-doped substrate with between 0.5 and 3 litres, preferably substantially 1.5 litres, between 25 and 100 mmol/l, preferably substantially 50 mmol/l of aqueous silicotungstic acid for surface fixation of the dehydration catalyst, preferably subsequent drying at between 60 and 120° C., preferably substantially 90° C., and preferably subsequent calcination at between 250 and 450° C., preferably substantially 350° C., for between 6 and 24 hours, preferably substantially 12 hours.

Using this production method and selecting substrates with the previously defined pore size, tests have shown that otherwise highly water-soluble catalysts, in particular dehydration catalysts such as silicotungstic acid, are immobilised on the catalyst substrate. This means that, during the reaction, which is carried out in liquid, aqueous phase and under the above-mentioned pressure, the dehydration catalyst cannot be dissolved by hydration, but remains stably immobilised and furthermore the active centres remain freely accessible. The immobilisation of the dehydration catalyst, in particular of silicotungstic acid, is most likely due to physicochemical interactions on the one hand (presumably of van der Waals forces with adsorptive effect) and the ideal pore diameter and thus the inaccessibility of the dehydration catalyst for hydration on the other hand.

An alternative possibility is the co-extrusion of the dehydration catalyst, for example silicotungstic oxides, directly into the support material, for example zirconium dioxide, so that the pore diameter does not have to be taken into account for subsequent impregnation. However, this alternative has proven to be very costly and complex.

The invention is further explained below on the basis of a preferred embodiment shown in the drawing, to which the invention should by no means be limited, however. The drawing shows, specifically:

FIG. 1 a preferred embodiment of the method and of the device for the catalytic conversion of a substance mixture containing glycerol to propanols in a fixed-bed reactor.

FIG. 1 shows a preferred embodiment of the device 1 for the catalytic conversion of a substance mixture containing glycerol to propanols in a fixed-bed reactor 2. In particular, crude glycerol that is removed from a storage container 3 is used as starting material. The substance mixture containing glycerol is then fed, preferably by means of a pump, to a filter device 4, in which it is filtered in order to remove any undissolved solids and undesirable accompanying substances which may be contained therein, depending on the quality of the substance mixture containing glycerol. In the specific embodiment, the filter device consists of two redundantly arranged, back-flushable filters, a control valve preferably being arranged upstream of each back-flushable filter. The filtered substance mixture containing glycerol is then mixed with water in a mixing vessel 5 and diluted, the resulting glycerol content preferably being between 10 and 60 percent. The mixing vessel 5 is equipped with a safety valve (pressure relief valve).

The filtered and diluted substance mixture containing glycerol is then heated via an economiser heat exchanger 6, to which the substance mixture containing glycerol has been fed via a pump, and then hydrogen is added in the static mixer 7, and the mixture is advantageously then passed through a cooler. This mixture is then fed to the continuous, catalytic fixed-bed reactor 2, which in turn preferably comprises a safety valve. The reacted substance mixture is fed via the line 8 for heat input in the heat exchanger 6. The energy of the process waste heat is sufficient to preheat the filtered and mixed substance mixture containing glycerol, and usually no external reaction energy needs to be supplied. Thus, the reaction is adiabatic. An exception to this is, of course, during the switch-on process.

The converted substance mixture is then fed via a flash valve to a separation device 9, in particular a vapour-liquid separator or flash drum, for the recovery of hydrogen from the substance mixture converted in the fixed-bed reactor.

The hydrogen recycling gas stream is passed through an air cooler, and highly volatile organic accompanying components recondense in the separator vessel. Subsequently, a part of the hydrogen recycling gas stream is flared downstream of a control valve for the discharge of by-product gases (in particular predominantly propane), the proportion of the flared hydrogen recycling gas stream being less than 0.5%, and particularly preferably less than 0.1%. The recovered hydrogen is then recompressed in a compressor 10 and added to the fresh hydrogen with which the substance mixture containing glycerol is mixed in the static mixer 7, the proportion of recycled hydrogen in the hydrogen input in one cycle preferably being between 70 and 97 percent. The pure propanols can then be obtained from the reacted substance mixture in a treatment cascade 11, to which the reacted substance mixture is fed via a heat exchanger and a cooler, and the extraction agents for the extraction circuit can be recovered in the same treatment cascade, and the process water for reuse in the production of a diluted substance mixture containing glycerol is also recovered, the recovered process water being mixed with fresh water in a water mixer 12 and then added to the substance mixture containing glycerol in the mixer 5. Preferably, the proportion of recovered process water makes up between 80 and 100 percent of the total water input of a cycle, even more preferably between 90 and 100 percent.

The reacted substance mixture fed to the treatment cascade 11 first passes through a control valve and is supplied to a separating device, to which toluene is fed as an extraction agent and in which the process water is separated from the reacted substance mixture, which is then fed to the water mixer 12 via a control valve, as already explained, with dirty water being removed via a further control valve. Furthermore, a mixture of propanols and toluene is fed from the separating device to a first extraction column, to which N-methyl-2-pyrrolidone (NMP) is added as an extraction agent. In this extraction column the top product containing the target fraction (propanols) is extracted at 108° C., and then the propanols are obtained via a condensation column at 30° C. Furthermore, a mixture of toluene and NMP is separated from the first extraction column, for example at a temperature of 160° C., via an evaporation column and fed to a second extraction column, for example at 134° C. In this second extraction column, the bottom product is drawn off and the residual toluene is distilled off and fed back to the second extraction column for energy input, and subsequently the unevaporated NMP is fed back again to the first extraction column at about 232° C. via a pump—mixed with fresh NMP in a static mixer—for precipitation of the propanols. In the second extraction column, the top product is also drawn off and the toluene is condensed out at below 125° C. and fed via a pump and in a static mixer mixed with fresh toluene from the separation device as an extraction agent.

The embodiment shown in the drawing and explained in conjunction with it serves to explain the invention and does not limit the invention. The temperatures stated in the embodiment are only to be understood as examples; other temperatures are possible.

The invention claimed is:

1. A method for the catalytic conversion of a substance mixture containing glycerol to propanols in a fixed-bed reactor, wherein substrates of the catalyst comprise inorganic materials and/or metal oxides, wherein the substrates comprise a pore diameter at the surface of between 10 and 25 angstroms, the catalyst comprising silicotungstic acid or phosphotungstic acid, wherein the catalytic conversion of the substance mixture containing glycerol to propanols takes place in liquid phase under a pressure of between 10 and 100 bar.

2. The method according to claim 1, wherein the substrates are extrudate pellets.

3. The method according to claim 1, wherein the reaction of the substance mixture containing glycerol takes place continuously in the fixed-bed reactor.

4. The method according to claim 1, wherein mixed oxides of silicon, tungsten, zirconium and/or aluminium.

5. The method according to claim 1, wherein the substance mixture containing glycerol is crude glycerol, technical glycerol or purified glycerol.

6. The method according to claim 1, wherein the method comprises one or more of the following steps:
removing the substance mixture containing glycerol from a storage container,
filtering the substance mixture containing glycerol and/or
mixing the substance mixture containing glycerol with water in the mixer, the concentration of the glycerol being adjusted to between 5 and 80 percent.

7. The method according to claim 1, wherein the method comprises one or more of the following steps:
heating the substance mixture containing glycerol with a heat exchanger,
adding hydrogen to the substance mixture containing glycerol
returning the heat of the substance mixture reacted in the fixed-bed reactor to the heat exchanger for heat transfer to the substance mixture containing glycerol before the reaction, so that the method is adiabatic.

8. The method according to claim 1, wherein hydrogen is recovered from the substance mixture reacted in the fixed-bed reactor via a separator device, the recovered hydrogen being recompressed subsequently in a compressor and added to fresh hydrogen, the recovered hydrogen having a proportion of between 50 and 99 percent of the total hydrogen used in the method.

9. The method according to claim 1, wherein propanols are obtained from the substance mixture reacted in the fixed-bed reactor, by first removing water from the substance mixture reacted in the fixed-bed reactor via a treatment cascade and obtaining pure propanols, the separated process water being added to a fresh water in a water mixer and the water mixture being used in the method at an earlier point, for mixing in the mixer, and the recovered process water having a proportion of between 80 and 100 percent of the total water used in the method and/or
longer-chain hydrocarbons are built up, from the substance mixture reacted in the fixed-bed reactor.

10. The method according to claim 1, wherein the reaction takes place in the fixed-bed reactor at a temperature between 150 and 300° C.

11. The method according to claim 1, wherein the reaction takes place in the fixed-bed reactor at a pressure of between 10 and 100 bar.

12. The method according to claim 2, wherein the substrates are ceramic.

13. The method according to claim 4, wherein zirconium dioxide, aluminosilicate zeolites and/or aluminophosphate zeolites are used as substrate of the catalyst.

14. The method according to claim 4, the aluminophosphate zeolites comprise VFI zeolites and/or VPI-5 zeolites, dealuminated USY zeolites and/or aluminium dioxide.

15. The method according to claim 4, wherein the catalyst comprises a platinum doping.

16. The method according to claim 6, wherein the step of filtering the substance mixture containing glycerol is practiced using undissolved solids and/or diluted accompanying substances contained therein being removed.

17. The method according to claim 6, wherein the concentration of the glycerol in the step of mixing the substance mixture containing glycerol with water in the mixer is adjusted to between 10 and 60 percent.

18. The method according to claim 6, wherein the concentration of the glycerol in the step of mixing the substance mixture containing glycerol with water in the mixer is adjusted to between 15 and 50 percent.

19. The method according to claim 7, wherein the step of heating the substance mixture containing glycerol is conducted with an economiser.

20. The method according to claim 7, wherein the step of adding hydrogen to the substance mixture containing glycerol is conducted in a static mixer.

\* \* \* \* \*